US008193136B2

(12) United States Patent
Taylor et al.

(10) Patent No.: US 8,193,136 B2
(45) Date of Patent: Jun. 5, 2012

(54) ANTIBACTERIAL COMPOSITIONS COMPRISING QUATERNARY AMMONIUM GERMICIDES AND ALKAMINE OXIDES HAVING REDUCED IRRITATION POTENTIAL

(75) Inventors: Timothy J. Taylor, Phoenix, AZ (US); Priscilla S. Fox, Phoenix, AZ (US); Kathleen Carmelle Cater, Phoenix, AZ (US)

(73) Assignee: The Dial Corporation, Scottsdale, AZ (US)

( * ) Notice: Subject to any disclaimer, the term of this patent is extended or adjusted under 35 U.S.C. 154(b) by 0 days.

(21) Appl. No.: 13/218,137

(22) Filed: Aug. 25, 2011

(65) Prior Publication Data

US 2011/0313049 A1    Dec. 22, 2011

Related U.S. Application Data

(63) Continuation of application No. 12/088,399, filed as application No. PCT/US2006/048991 on Dec. 20, 2006, now abandoned.

(60) Provisional application No. 60/755,569, filed on Dec. 30, 2005.

(51) Int. Cl.
*C11D 1/75* (2006.01)
*C11D 1/835* (2006.01)
*C11D 1/62* (2006.01)

(52) U.S. Cl. ........ 510/124; 510/119; 510/123; 510/130; 510/131; 510/421; 510/422

(58) Field of Classification Search .................. 510/119, 510/123, 124, 130, 131, 421, 422
See application file for complete search history.

(56) References Cited

U.S. PATENT DOCUMENTS

| 6,159,924 | A  | * | 12/2000 | Weller et al. ............... 510/384 |
| 6,425,406 | B1 | * | 7/2002  | Klinkhammer et al. ... 134/22.19 |
| 2001/0044393 | A1 | * | 11/2001 | Peterson et al. ............. 510/130 |
| 2003/0022941 | A1 | * | 1/2003  | Taylor et al. ............... 514/642 |
| 2003/0073600 | A1 | * | 4/2003  | Avery et al. ............... 510/382 |
| 2003/0083224 | A1 | * | 5/2003  | Wick et al. ............... 510/499 |
| 2003/0096725 | A1 | * | 5/2003  | Tsibouklis et al. .......... 510/421 |
| 2006/0111265 | A1 | * | 5/2006  | Rypkema et al. ............. 510/504 |

\* cited by examiner

*Primary Examiner* — Charles Boyer
(74) *Attorney, Agent, or Firm* — David K. Benson

(57) ABSTRACT

Antibacterial compositions having antibacterial effectiveness and reduced eye irritation potential are disclosed. The antibacterial compositions contain a quaternary ammonium compound, an alkamine oxide, a nonionic compound, optional adjuvant materials known in the art, and water. The eye irritation is decreased by decreasing the amount, by weight, of alkamine oxide present in the composition and alternatively, or in combination therewith, increasing the ratio of nonionic material to alkamine oxide present in the composition.

9 Claims, No Drawings

ANTIBACTERIAL COMPOSITIONS COMPRISING QUATERNARY AMMONIUM GERMICIDES AND ALKAMINE OXIDES HAVING REDUCED IRRITATION POTENTIAL

CROSS-REFERENCE TO RELATED APPLICATIONS

This application is a continuation of U.S. patent application Ser. No. 12/088,399, which was filed on Aug. 3, 2009 and was a U.S. National Phase filing under 35 U.S.C. 371 claiming priority to PCT Application No. PCT/US2006/048991, which was filed on Dec. 20, 2006, which application in turn claims priority to U.S. Provisional Patent Application Ser. No. 60/755,569, which was filed Dec. 30, 2005, all of which are incorporated herein by reference.

FIELD OF INVENTION

The present invention relates generally to antibacterial compositions exhibiting the antibacterial effectiveness of quaternary ammonium compounds and reduced irritation to mammalian tissue.

BACKGROUND

Antibacterial personal care compositions are known in the art. Especially useful are antibacterial cleansing compositions, which typically are used to cleanse the skin and to destroy bacteria and other microorganisms present on the skin, especially the hands, arms, and face of the user. Several different classes of antibacterial agents have been used in antibacterial cleansing compositions. One such agent, quaternary ammonium compounds, are effective cleansing agents, however, these compounds can cause irritation to the epithelial tissue of the user, particularly the skin and eye tissue.

Various attempts have been made to mitigate the irritation of quaternary ammonium compounds to the skin and eye. Mitigants have included combining quaternary ammonium compounds with nonionic compounds, maltodextrin, urea, benzoate salts, and ethoxylated lanolin or alkoxylated fatty amines. Another mitigant found capable of decreasing irritation has been to combine quaternary ammonium compounds with mixtures of alkamine oxide surfactants with nonionic materials.

While these mitigants provide some comfort to the consumer, a need exists for a phase stable, effective quaternary ammonium germicide that effectively and sufficiently reduces irritation to animal tissue, particularly skin and eye tissue.

SUMMARY OF THE INVENTION

This summary of the invention is intended to introduce the reader to various exemplary aspects of the invention. Particular aspects of the invention are shown in other sections hereinbelow, and the invention is set forth in the appended claims which alone demarcate its scope.

In accordance with an exemplary embodiment of the present invention, an antibacterial composition that exhibits reduced eye irritancy is provided. The antibacterial composition comprises a quaternary ammonium compound, an alkamine oxide, a nonionic material and water. The quaternary ammonium compound preferably is present in the amount of from about 0.1% to about 5.0% by weight of the composition.

The alkamine oxide is preferably present in an amount of from about 0.1% to about 10% by weight of the composition. The nonionic material is preferably present in an amount from about 0.3% to about 1.5% by weight of the composition.

In an exemplary embodiment of the invention, an antibacterial composition is provided wherein the nonionic material is present such that the relative weight ratio of the nonionic material to the alkamine oxide, by weight, yields a Permeability Value in the Bovine Corneal Opacity and Permeability assay of less than 1.2 while maintaining antibacterial efficacy.

DETAILED DESCRIPTION OF THE INVENTION

The following description is of exemplary embodiments only and is not intended to limit the scope, applicability or configuration of the invention in any way. Rather, the following description provides convenient illustrations for implementing various embodiments of the invention. Various changes to the described embodiments may be made in the function and arrangement of the elements described without departing from the spirit and scope of the invention.

In accordance with an exemplary embodiment of the present invention, the antibacterial composition includes a quaternary ammonium compound, an alkamine oxide, a nonionic material, and water and exhibits reduced irritation to animal tissue.

In a preferred embodiment of the invention, the quaternary ammonium compound is present in the amount of about from 0.1 to 5.0% by weight of the composition. For example, in various exemplary embodiments, the quaternary ammonium compound is benzethonium chloride or benzalkonium chloride. For example, in a benzethonium chloride embodiment, the benzethonium chloride is present in the composition in the amount of about 1.0% by weight.

In accordance with various embodiments, the amount of alkamine oxide surfactant present in the composition is related to the amount and identity of the antibacterial agent in the composition, to the identity of the alkamine oxide surfactant, and the end use of the composition. In a preferred embodiment of the invention, the alkamine oxide is present in the amount of from about 0.1 to about 10% by weight. In one exemplary embodiment, the alkamine oxide is lauramine oxide. In various exemplary embodiments, depending upon the specific composition, the lauramine oxide is present in varying amounts ranging, preferably, from about 0.3% to about 1.5% by weight.

In accordance with various embodiments, an alkamine oxide useful in the present invention contains at least one long hydrocarbon chain containing at least eight carbon atoms. One class of amine oxides is the alkyl di(lower alkyl) amine oxides, wherein the alkyl group contains 8 to 22, and preferably about 10 to about 16, carbon atoms, and can be straight or branched chain, saturated or unsaturated. The lower alkyl groups contain 1 to 7 carbon atoms, and typically are methyl. Specific examples include, but are not limited to, lauryl dimethyl amine oxide, myristyl dimethyl amine oxide, dimethyl cocoamine oxide, dimethyl (hydrogenated tallow)amine oxide, myristyl/palmityl dimethyl amine oxide, myristyl/lauryl dimethyl amine oxide, cetyl dimethyl amine oxide, stearyl dimethyl amine oxide, and myristyl/cetyl dimethyl amine oxide.

Another class of useful amine oxides includes alkyl di(hydroxy lower alkylamine oxides in which the alkyl group contains 8 to 22, and preferably about 10 to about 16 carbon atoms, and can be straight or branched chain, saturated or unsaturated. Specific examples, include, but are not limited to, bis(2-hydroxyethyl)cocoamine oxide, bis(2-hydroxyethyl)tallow amine oxide, and bis(2-hydroxyethyl)stearylamine oxide.

Additional useful amine oxides are termed alkamidopropyl di(lower alkyl)amine oxides in which the alkyl group contains 8 to 22, and preferably about 10 to about 16 carbon atoms, and can be straight or branched chain, saturated or unsaturated. Examples are cocoamidopropyl dimethyl amine oxide and tallowamidopropyl dimethyl amine oxide. Further useful amine oxides are termed alkylmorpholine oxides in which the alkyl group contains 8 to 22, and preferably about 10 to about 16, carbon atoms, and can be straight or branched chain, saturated or unsaturated. Alkamine oxides are commercially available, for example, from Stepan Co., Northfield, Ill., and Lonza Inc., Fairlawn, N.J.

The above classes of alkamine oxide surfactants contain a C8-C22 alkyl group selected from, for example, octyl, decyl, undecyl, lauryl, tridecyl, myristyl, cetyl, stearyl, isostearyl, oleyl, and mixtures thereof. Examples of amine oxide surfactants include, but are not limited to, decyl dimethylamine oxide, lauryl dimethylamine oxide, stearyl dimethylamine oxide, oleyl dimethylamine oxide, coco dihydroxyethylamine oxide, cetyl N,N-dihydroxyethylamine oxide, oleyl N,N-dihydroxyethylamine oxide, cocamine oxide, cocamidopropylamine oxide, lauramidopropylamine oxide, oleamine oxide, oleamidopropylamine oxide, wheat germamidopropylamine oxide, isostearamido-propylamine oxide, stearamine oxide, stearamido-propylamine oxide, cocomorpholine oxide, decylamine oxide, dihydroxyethyl C 8-C 10 alkoxypropylamine oxide, dihydroxyethyl C9-C11 alkoxypropylamine oxide, dihydroxyethyl C12-C11 alkoxypropylamine oxide, dihydroxyethyl cocamine oxide, dihydroxyethyl stearamine oxide, dihydroxyethyl tallowamine oxide, hydrogenated tallow amine oxide, hydroxyethyl hydroxypropyl C 12-C 15 alkoxypropylamine oxide, isostearamidopropyl morpholine oxide, myristamidopropylamine oxide, myristamine oxide, palmitamidopropylamine oxide, palmitamine oxide, PEG-3 lauramine oxide, tallow amidopropylamine oxide, tallow amine oxide, undecylenamidopropylamine oxide, and mixtures thereof. Preferred alkamine oxide surfactants are the alkyl di(lower alkylamine oxides in which the alkyl group contains about 12 to about 16 carbon atoms, including lauramine oxide, myristamine oxide, cocamine oxide, cetamine oxide, and mixtures thereof.

In accordance with other embodiments of the invention, the composition contains a blend of alkamine oxide surfactants. In most preferred embodiments, a first component of the alkamine oxide blend contains twelve or fewer carbon atoms and a second component contains more than twelve carbon atoms.

In a preferred embodiment of the invention, a nonionic material is present in the composition so that the ratio of nonionic material to alkamine oxide by weight yields a composition with a Permeability Value (PERMV) in a Bovine Corneal Opacity and Permeability (BCOP) assay of less than about 1.2. In an exemplary embodiment, the nonionic material is a nonionic polymeric surfactant like a copolymer comprised of a block copolymer of ethylene oxide and propylene oxide or an alkylpolyglucoside surfactant. In another exemplary embodiment, the nonionic material is decyl polyglucose (APG) present in the composition at an amount of about 2.5% by weight. In another exemplary embodiment, the nonionic material is Pluronic F108 present in the composition at an amount of about 2.5%.

In accordance with various embodiments of the invention, the composition optionally includes polymeric thickeners of the nonionic or cationic class, dyes, perfumes, builders, pH adjusters, solvents, and other adjuvant materials. For example, in an exemplary embodiment of the present invention, a polymeric thickener, Natrosol 250HHR CS, is included in the composition at an amount of about 1.0% by weight.

In one embodiment of the composition, the pH of the composition is between about 5 and 9, preferably between about 6 and 8, and most preferably between about 6.5 and 8.

In a still further exemplary embodiment of the invention, the antibacterial composition may be free anionic or zwitterionic surfactants including sulfates, sulfonates, carboxylates, and aminocarboxylates.

The antibacterial effectiveness of various formulations of the compositions formed in accordance with the present invention were tested by conducting a Health Care Personnel Hand Wash test, an in vivo test of efficacy, whereby the survival of challenged organisms exposed to antibacterial test formulation is determined as a function of the number of hand washes. In general, the Health Care Personnel Hand Wash test is well known in the antibacterial products industry. In this test, hands of volunteers are inoculated with a volume of bacterial inoculum to constitute a bacterial challenge to the hands. The volunteers then wash their hands with the antibacterial composition to be tested, and this cycle is repeated 11 times. Bacterial reductions are determined after the first and eleventh wash.

In this example, two exemplary formulations of antibacterial compositions were tested using the Health Care Personnel Hand Wash test. Hibiclens, a commercial product, serves as a positive control in the test. Table 1 summarizes the compositions of the formulations, Formulation 1 and 2.

TABLE 1

|  | Formulation 1 | Formulation 2 |
|---|---|---|
|  | weight percent | |
| Deionized Water | 90.24 | 91.54 |
| Natrosol 250HHR CS | 1.0 | 1.0 |
| Benzethonium Chloride | 1.0 | 1.0 |
| Pluronic F108 | 2.5 | 0.0 |
| Lauramine Oxide | 1.5 | 0.3 |
| Decyl Polyglucose (APG) | 0.0 | 2.5 |
| Sodium Phosphate, 10% sol. | 0.26 | 0.46 |
| Total | 100.0 | 100.0 |
| Final pH | 7.45 | 7.49 |
| Ratio of Nonionic:active basis of Lauramine Oxide | 1.7:1 | 8.3:1 |

Table 2 summarizes the antibacterial performance of these formulations as measured by the Health Care Personnel Hand Wash test:

TABLE 2

| | Log10 Bacterial Reduction | | | | | |
|---|---|---|---|---|---|---|
| | Wash 1 | | | Wash 11 | | |
| Formulation | Formula | Placebo | Hibiclens (+ control) | Formula | Placebo | Hibiclens (+ control) |
|---|---|---|---|---|---|---|
| 1 | 2.49 | 2.04 | 2.7 | 3.02 | 2.62 | 3.52 |
| 2 | 2.53 | 1.77 | 3.27 | 3.13 | 1.90 | 4.30 |

The above results illustrate the enhanced antibacterial effectiveness of antibacterial compositions formed in accordance with various embodiments of the present invention. Both formulations achieved log reductions of greater than 2 on the first wash and greater than 3 on the 11th wash. Additionally, both formulations exhibit superior antibacterial effectiveness as compared to the placebo. Thus, both formulations produce a preferred log reduction and provide sufficient performance.

The reduced potential for eye irritation of various formulations of the compositions formed in accordance with the present invention was conducted using a Bovine Corneal Opacity and Permeability (BCOP) assay. The BCOP assay is known in the consumer products industry as an in vitro test for eye irritation potential. For surfactant-based formulations, the Permeability Value (PERMV) is also a measure of potential irritancy in the BCOP assay. Specifically, the Permeability Value is the Optical Density at 490 nm (OD490) determined with a spectrophotometer. It is used to measure the potential for eye irritation with higher irritation potential corresponding to higher Permeability Values. For personal cleansing compositions like liquid hand soaps, shower gels, and the like, an appropriate harsh control (control with high known potential for eye irritation) has a (PERMV) of 1 or higher. For example, a commercial liquid hand soap that is recognized as having potential for causing eye irritation has a (PERMV) of 1 to 1.125 in the BCOP assay. In general, compositions with PERMVs less than 1 are preferred in the art.

In this example, various embodiments of antibacterial compositions were tested using the BCOP assay. Table 3 summarizes the base formulation used while varying the ratio of nonionic material to lauramine oxide and measuring the resulting PERMV score.

TABLE 3

| Base Formulation | |
|---|---|
| | weight percent |
| Deionized Water | Variable |
| Natrosol 250HHR CS | 1.0 |
| Benzethonium Chloride | 1.0 |
| Lauramine oxide | 0.3% or 1.5% |
| Nonionic material (Pluronic F108 or decyl polyglucoside) | variable |
| Total | 100% |

Table 4 summarizes the impact of the ratio of decyl polyglucoside to lauramine oxide (N:A) on PERMV in the BCOP assay.

TABLE 4

| Lauramine oxide 1.5%, by weight | | Lauramine oxide 0.3%, by weight | |
|---|---|---|---|
| N:A | PERMV | N:A | PERMV |
| 0:1 | 1.776 | 0:1 | 0.854 |
| 1.7:1 | 1.784 | 6.8:1 | 0.437 |
| 2:1 | 1.533 | 8.3:1 | 0.66* |
| 3:1 | 1.971 | 8.5:1 | 0.812 |

*Formulation 2, as above

Table 4 reveals that lauramine oxide is a key determinant of PERMV values. Lower lauramine oxide levels leads to lower PERMV, and hence lower eye irritation potential. Additionally, this example illustrates the surprising discovery that increasing the N:A ratio leads to lower PERMV, and hence decreasing eye irritation potential, especially for compositions with lower amounts of lauramine oxide.

Table 5 summarizes the impact of the ratio of Pluronic F108 to lauramine oxide (N:A) on PERMI in the BCOP assay.

TABLE 5

| Lauramine oxide 1.5%, by weight | | Lauramine oxide 0.3%, by weight | |
|---|---|---|---|
| N:A | PERMV | N:A | PERMV |
| 0:1 | 1.776 | 0:1 | 0.854 |
| 1.7:1 | 1.342 | 8.3:1 | 0.660 |
| 1.7:1 | 1.124* | 8.5:1 | 0.532 |
| 3:1 | 1.123 | | |
| 5:1 | 0.643 | | |
| 7:1 | 0.587 | | |

*Formulation 1, as above

Table 5 also demonstrates that lauramine oxide is the main determinant of PERMV values. Surprisingly however, the PERMV scores, and the potential fore eye irritation, decrease strongly with increasing N:A, even for formulations with high lauramine oxide content. Without being limited by any particular theory, amine oxides appear to be the major determinants of irritation in formulations with quaternary ammonium germicides. Surprisingly, the ratio of nonionic material to amine oxide can be used to manipulate the irritation potential of formulations while maintaining antimicrobial efficacy at constant germicide concentration.

Many modifications and variations of the invention as set forth can be made without departing from the spirit and scope thereof, and therefore only such limitations should be imposed as are indicated by the appended claims.

What is claimed is:

1. A method of washing the skin of a human, comprising:
    washing the skin with an antibacterial composition, which comprises
        a quaternary ammonium compound present in the amount of from about 1 to about 5 percent by weight of the antibacterial composition,
        one or more alkamine oxides present in the amount of from about 0.1 to about 10 percent by weight of the antibacterial composition,
        one or more nonionic materials comprising a block copolymer of ethylene oxide and propylene oxide,
        one or more liquid carriers, and
        optionally one or more ingredients selected from a group comprising:
    polymeric thickeners of the nonionic or cationic class, dyes, perfumes, builders, pH adjusters, solvents, and mixtures thereof,
        wherein the antibacterial composition is substantially free of anionic surfactants and has a relative weight ratio of the nonionic material to the one or more alkamine oxides of from about 5:1 to about 8.5:1; and
    rinsing the antibacterial composition from the skin.

2. The method according to claim 1, wherein said quaternary ammonium compound is selected from the group consisting of: benzethonium chloride, benzalkonium chloride, alkyl dimethylbenzyl ammonium chloride, cetyl trimethyl ammonium chloride.

3. The method according to claim 1, wherein said one or more alkamine oxides are present in the amount of from about 0.3 to about 1.5 percent by weight of the antibacterial composition.

4. The method according to claim 1, wherein said alkamine oxide is lauramine oxide.

5. The method according to claim 1, wherein said nonionic material further comprises an alkylpolyglucoside surfactant.

6. The method according to claim 1, wherein said nonionic material is Pluronic F108 and further comprises decyl polyglucose.

7. The method according to claim 1, wherein the antibacterial composition has a pH between about 6.5 and 8.

8. The method according to claim 1, wherein the relative weight ratio of the nonionic material to the alkamine oxide yields a composition with a Permeability Value in a BCOP assay of less than about 1.2.

9. The method according to claim 1, wherein said composition is free of anionic and zwitterionic surfactants.

* * * * *